(12) United States Patent
Kil et al.

(10) Patent No.: US 7,725,329 B2
(45) Date of Patent: May 25, 2010

(54) SYSTEM AND METHOD FOR AUTOMATIC GENERATION OF A HIERARCHICAL TREE NETWORK AND THE USE OF TWO COMPLEMENTARY LEARNING ALGORITHMS, OPTIMIZED FOR EACH LEAF OF THE HIERARCHICAL TREE NETWORK

(75) Inventors: David H. Kil, Prospect, KY (US); David B. Pottschmidt, New Albany, IN (US)

(73) Assignee: Humana Inc., Louisville, KY (US)

( * ) Notice: Subject to any disclaimer, the term of this patent is extended or adjusted under 35 U.S.C. 154(b) by 1429 days.

(21) Appl. No.: 11/114,692

(22) Filed: Apr. 26, 2005

(65) Prior Publication Data

US 2005/0240544 A1 Oct. 27, 2005

Related U.S. Application Data

(60) Provisional application No. 60/565,579, filed on Apr. 27, 2004.

(51) Int. Cl.
*G06Q 10/00* (2006.01)
*G06F 19/00* (2006.01)
*G06Q 40/00* (2006.01)

(52) U.S. Cl. .................................. 705/2; 705/3; 705/4
(58) Field of Classification Search .................. 705/2–4
See application file for complete search history.

(56) References Cited

U.S. PATENT DOCUMENTS 6,658,396 B1   12/2003   Tang et al.

2002/0069079 A1   6/2002   Vega

OTHER PUBLICATIONS

International Search Report, Form PCT/ISA/210, 2 pages, for International Application No. PCT/US05/14522 completed on Sep. 28, 2006 and mailed Feb. 9, 2007.
L. Anderson and J. Minnich, "Small Group Renewal Underwriting Using the Ingenix Predictive Model," 2001, Ingenix, Inc.
F. Foresee and M. Hagan, "Gauss-Newton Approximation to Bayesian Learning," 1997, Proc. International Joint Conference on Neural Networks.
T. Hastie and R. Tibshirani, "Discriminant Adaptive Nearest Neighbor Classification," IEEE Trans. PAMI, Jun. 1996, pp. 607-615, vol. 18, No. 6.
D. Kil and F. Shin, "Pattern Recognition and Prediction with Applications to Signal Characterization," 1996, pp. 119-143, AIP Press, New York, NY.
A. Neumaier, "Solving Ill-Conditioned and Singular Linear Systems: A Tutorial on Regularization," SIAM Review, 1998, pp. 636-666, vol. 40.
J. Rissanen, "Stochastic Complexity in Statistical Inquiry," World Scientific, 1989, pp. 79-93, River Edge, NJ.

*Primary Examiner*—Robert W Morgan
*Assistant Examiner*—Joseph Burgess
(74) *Attorney, Agent, or Firm*—James C. Eaves, Jr.; Greenbaum Doll & McDonald PLLC (57) ABSTRACT

A system and method that generates a hierarchical tree network and uses linear-plus-nonlinear learning algorithms to form a consensus view on a member's future health status. Each leaf in the hierarchical tree network is homogeneous in clinical characteristics, experience period, and available data assets. Optimization is performed on each leaf so that features and learning algorithms can be tailored to local characteristics specific to each leaf.

13 Claims, 7 Drawing Sheets

SYSTEM AND METHOD FOR AUTOMATIC GENERATION OF A HIERARCHICAL TREE NETWORK AND THE USE OF TWO COMPLEMENTARY LEARNING ALGORITHMS, OPTIMIZED FOR EACH LEAF OF THE HIERARCHICAL TREE NETWORK

This application claims the benefit of U.S. provisional patent application Ser. No. 60/565,579, filed on Apr. 27, 2004, for a system and method for automatic generation of a hierarchical tree network and the use of two complementary learning algorithms, optimized for each leaf of the hierarchical tree, incorporated herein by reference.

BACKGROUND OF THE INVENTION

Field of the Invention

The present invention relates to a system and method that generates a hierarchical tree network and uses linear-plus-nonlinear learning algorithms to form a consensus view on a member's future health status. Each leaf in the hierarchical tree network is homogeneous in clinical characteristics, experience period, and available data assets. Optimization is performed on each leaf so that features and learning algorithms can be tailored to local characteristics specific to each leaf.

SUMMARY OF THE INVENTION

The present invention is for a method for predicting a person's future health status. The method includes the steps of:

a. establishing a hierarchical tree network that, for a plurality of members, assigns each member to at most only one of a plurality of nodes as a function of a plurality of stratification variables;

b. providing to a computer based system, for the plurality of members and for each member, member demographic data, available member medical claim data, and available member pharmacy claim data;

c. performing feature selection for each of the plurality of nodes to identify for each node an optimal subset of features from a set comprising at least some of the member demographic data, available member medical claim data, and available member pharmacy claim data for all members assigned to that node;

d. training a MVLR algorithm and a BRN algorithm using at least some of the member demographic data, available member medical claim data, and available member pharmacy claim data and storing learned parameters in a database to create a learned parameter database;

e. using the learned parameter database and, for at least one member, using that at least one member's member demographic data, available member medical claim data, and available member pharmacy claim data, calculating a MVLR future health status score using the MVLR algorithm and calculating a BRN future health status score using the BRN algorithm, and calculating an arithmetic mean of the MVLR future health status score and the BRN future health status score to determine a final score.

The stratification variables can include the member's enrollment duration, for example, less than six months or at least six months; the presence or lack of a catastrophic condition; the presence or lack of diabetes; the presence of either a pharmacy trigger or an inpatient admission trigger; and the presence of both medical and pharmacy claim data, the presence of only pharmacy claim data, or the presence of only medical claim data.

The method can also include a reporting step, where information about the member, along with the calculated final score is presented. For example, the member information may include enrollment/eligibility information, clinical condition information including conditions, trigger types and trigger dates, and representations of member costs over time for pharmacy and/or medical claims.

BRIEF DESCRIPTION OF THE DRAWINGS

A better understanding of the present invention will be had upon reference to the following description in conjunction with the accompanying drawings, wherein:

FIGS. 6 A-F show plots of the square root of one-year future cost versus various covariates. These simple plots provide a lot of useful insight. If there is a simple linear relationship, one will see a straight, monotonically increasing line. Unfortunately, we don't see such an obvious trend with any of these features, indicating that there is no simple linear insight.

DETAILED DESCRIPTION OF THE PREFERRED EMBODIMENT

As background, predictive models used in the health-insurance industry attempt to predict a member's future health status. They can be deployed in actuarial underwriting and identification of high-risk members for proactive clinical intervention.

Constructing a predictive model entails two stages, first, transforming claims data into a set of clinical features, and second, learning the relationship between clinical features (x) and future health status (y) using historical claims data. Typical clinical features include binary clinical markers. It is noted that IHCIS uses over several hundred binary clinical markers as covariates in a predictive model. Examples of binary markers are inpatient episode during the last 3 months, coronary artery bypass graft (CABG) procedure during the past year, heart attack during the past year, age, gender, past-year Rx cost, past-year medical cost, hospital length of stay, the number of emergency-room (ER) visits, Rx-to-med cost ratio, and so forth.

Learning algorithms deployed today encompass rule-based expert system (Active Health), linear regression (IHCIS, Ingenix, DxCG, Active Health, and Biosignia), multilayer perceptron (McKesson, classification-and-regression trees (CART)(Medical Scientists), and variants of instancebased learners, such as k-nearest or discriminant adaptive nearest neighbor (Hastie and Tibshirani, 1996)(MedAI). A learning algorithm attempts to find relationships between inputs and outputs by optimizing an objective function dominated by various forms of error terms, such as L-1 (absolute error), L-2 (mean-squared error), and L-∞ (maximum error) norms.

Conceptually, feature extraction and optimization facilitate learning by virtue of finding the smallest feature dimension that can adequately capture all the useful information present in raw data. Learning is analogous to finding a mapping function between optimal features and desired outputs. Learning algorithms can be broadly categorized into parametric, nonparametric, and boundary-decision types (Kil and Shin, 1996).

Parametric algorithms make strong parametric assumptions about data distribution, such as linear Gaussian. Simple parametric assumptions with the correspondingly small number of model parameters to tune can be a double-edged sword. If the actual data distribution is far more complex than the original assumption, then a parametric learner suffers from large model mismatch, which occurs when a learning algorithm is inadequate in capturing highly nonlinear relations between x and y. Paradoxically, in the presence of large data mismatch, which occurs frequently when the real-world data is rather different from the training data with which the model was tuned, simple parametric algorithms tend to outperform their nonparametric counterparts.

Nonparametric and boundary-decision learning algorithms attempt to learn data distribution from data. In general, neural networks and nonparametric learning algorithms, while good at minimizing model-mismatch errors, tend to be esoteric and obtuse. There is no simple way to explain the relationship between inputs and outputs. One can't say that higher prior-year medical cost leads to higher future cost because there is no such simple linear relationship. These learning algorithms have a large number of tunable parameters that can help capture complex, nonlinear relations. Unfortunately, such fine-tuning can also lead to overfitting or memorization, which can be dangerous in the presence of data mismatch. Further, nonlinear algorithms are notorious for their tendency to produce wild results when operating outside the trained space. That is, they are ill-suited when one expects large discrepancies between the real-world data and the training data with which the models were tuned.

Hidden Markov models are useful in modeling temporal transitions. In the real-world applications, it is frequently observed that computationally expensive Baum-Welch optimization is inferior to segmental k-means (SKM) despite higher advertised accuracy with the former. The reason is the trade off between model and data mismatch. In most real-world problems that I've seen, data mismatch is far more important than model mismatch.

Figure 1:
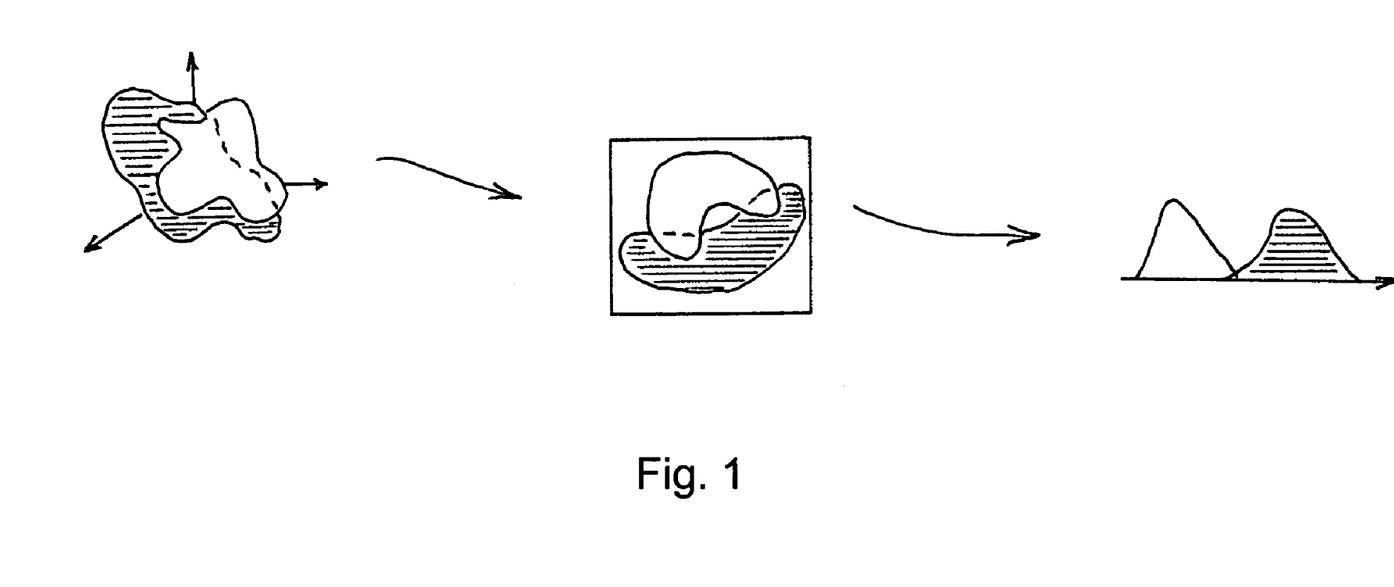
FIG. 1 shows an N-dimensional vector space processed and mapped to support a discussion of feature optimization and learning along with relative merits and weaknesses of various learning algorithms.

From left to right, to demonstrate the core concept of feature optimization and learning, FIG. 1 shows an original N-dimensional vector space spanned by raw data with a lot of overlap being signal processed and having the features ranked to produce the M-dimensional vector space spanned by good features determined after feature optimization, where M<<N, with a mapping on the right showing a final one-dimensional decision space created by a classifier. The following summarizes the relative merits and weaknesses of various learning algorithms. The characteristics of parametric learning algorithms are that they make strong parametric assumptions on the underlying class-conditional probability distribution, are very simple to train, and are susceptible to model mismatch. Examples of parametric learning algorithms are Multivariate Gaussian classifier, Gaussian mixture model, and linear regression. The characteristics of non-parametric learning algorithms are that they make no parametric assumption, learn distribution from data, are expensive to train in most instances, and are vulnerable to data mismatch between training and test data sets. Examples of non-parametric learning algorithms are Kernel estimator, Histogram, Functional form, and K-nearest. The characteristics of boundary decision learning algorithms are that they construct (non)linear boundary functions that separate multiple classes, are very expensive to train, and internal parameters are determined heuristically in most instances. Examples of boundary decision learning algorithms are multi-layer preceptron, discriminant neural network, and support vector machine.

The popularity of linear regression stems from its intuitive power. Let y denote the future cost and x clinical features or covariates $\in R^N$. Linear regression estimates y using the following equation:

$$\hat{y} = a_0 + \sum_{n=1}^{N} a_n x_n,$$

where $a_n$ denotes the direction and strength of correlation between $x_n$ and y. Let us illustrate the intuitive nature of linear regression. If the regression coefficient a for prior-year medical cost is +1.3, one can surmise that the future cost is likely to be 1.3 times the prior-year medical cost given all the other input variables are identical.

Despite its ease of interpretation, linear regression can't model complex, nonlinear relations by virtue of its simple mathematical formulation, which can lead to large model-mismatch errors. Nevertheless, the unanswered question is how to combine the strengths of linear and nonlinear models such that we can minimize both data- and model-mismatch errors.

In summary, the success of modeling hinges on the trade off between model mismatch and data mismatch. There is an urgent need to find an integrated, complementary set of algorithms in data transformation, extraction of derived features, optimization, and robust learning.

Figure 2:
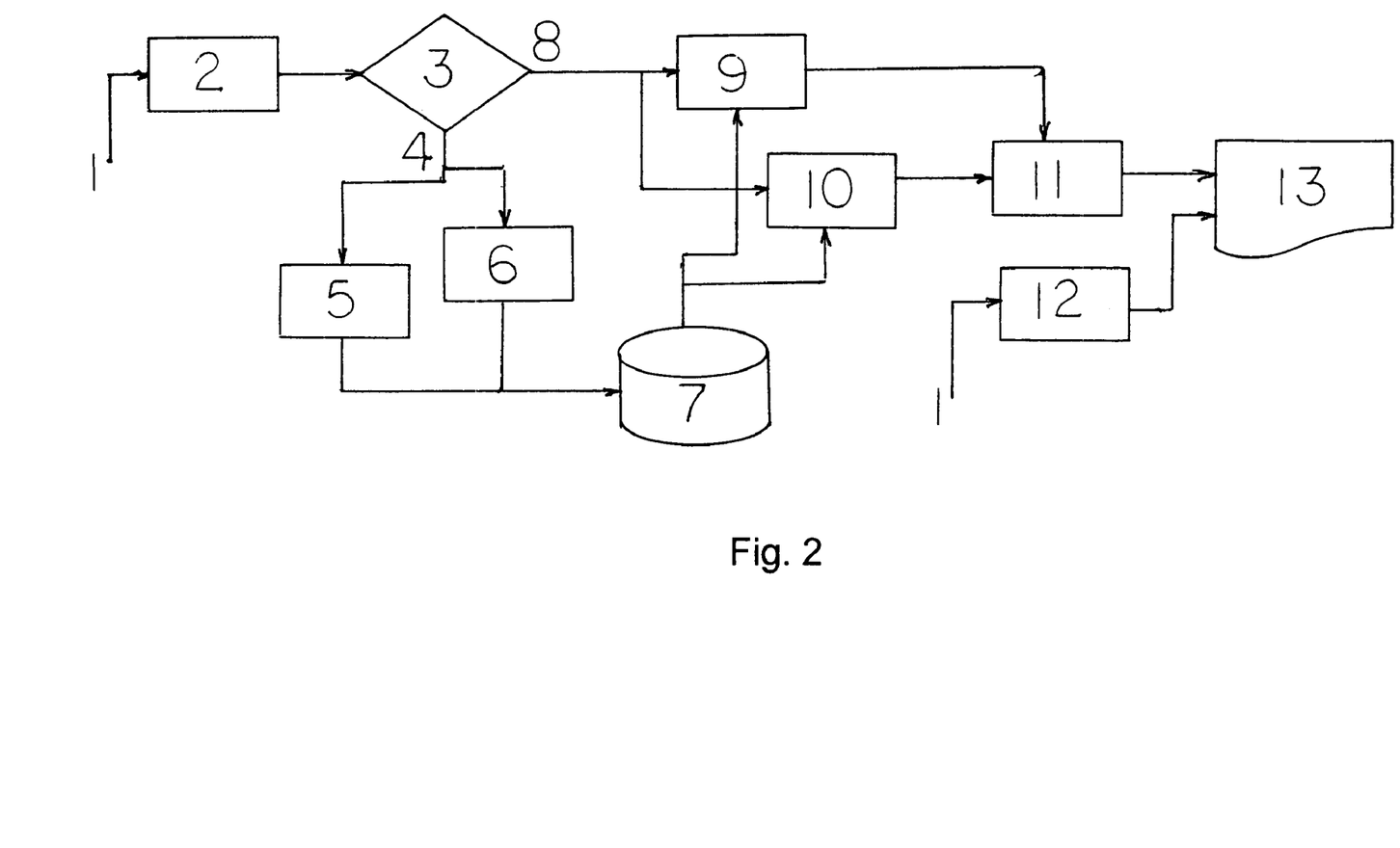
FIG. 2 shows the overall flowchart of hierarchical tree network generation, feature optimization, learning, and scoring.

For this invention, instead of trying to solve the entire problem in one broad stroke, we rely on a judicious divide-and-conquer approach. First, we divide the problem space into multiple logical subspaces using a hierarchical tree network. Each leaf of the hierarchical tree network is homogeneous in clinical characteristics, experience period, and available data assets. Furthermore, the hierarchical tree construction method is flexible enough to accommodate additional dimensions, such as clinical condition score representing a member's total disease burden, prior-experience characteristics (per-month prior cost), the ratio of chronic to total cost, and disease trajectories (increasing, decreasing, or stationary over time). Next feature ranking takes place in each leaf to exploit locally unique characteristics useful for prediction. Finally multiple learning algorithms investigate the relationship between the optimal feature subset and the output using their own thinking hats. FIG. 2 shows one embodiment of the divide-and-conquer approach.

Now we describe each step in detail.

Hierarchical tree network generation: Design a hierarchical tree network, where each leaf represents a clinically homogeneous cluster sharing similar Humana age and data flag. The clustering will be performed in the 2-D space of Clinical Condition Score (CCS) on the x axis and per-month prior cost on the y axis. Clinical condition score for the mth member with multiple co-morbid conditions is defined as follows:

$$CCS(m) = \sum_{k=1}^{N_{chr}+1} b_k(m)\sqrt{pppm(k)},$$

where $b_k(m)$ is the kth-condition presence/absence flag for the mth member and pppm(k) represents the average per-month cost for all the members with the kth co-morbid disease set. In this two-dimensional vector space, the first quadrant represents critically ill population with high per-member-per-month (PMPM) prior cost. The third quadrant represents relatively healthy population with low PMPM. The second quadrant contains members with a relatively small number of critical clinical conditions, but with large PMPM (perhaps behavioral issues). Finally, the fourth quadrant represents members with numerous critical clinical conditions, but with small PMPM, perhaps because they self-manage their conditions better.

a. Guidance for tree subdivision: Before-and-after entropy reduction measure (that is, do we gain anything by partitioning?), the level of data mismatch (MVLR performance difference between full-data-set training and ten-fold cross validation), minimum population size of 300, and necessity (enrollment duration and data availability).

b. Branch recombination: Recombination with nodes at different branches based on a similarity metric, such as Kullback-Leibler divergence defined as $$D_{KL}(i, j) = \int p(y \mid leaf = i) \ln\left(\frac{p(y \mid leaf = i)}{p(y \mid leaf = j)}\right) dy - \int p(y \mid leaf = j) \ln\left(\frac{p(y \mid leaf = j)}{p(y \mid leaf = i)}\right) dy,$$

where p(y|leaf=j) is the probability of the selected output associated with the hierarchical tree leaf j.

c. Approximation: Given the realities of our data, we use the following five features for creating hierarchical tree leaves:

1. Humana membership duration: This indicates how long a member has been with Humana, and determines the amount of claims history available. This field is necessary to account for business realities of high turnover rate in the health insurance industry.

2. Catastrophic condition: This field indicates the presence of expensive chronic conditions that require coordinated care management and rigorous clinical intervention.

3. Diabetes flag: Since the Personal Nurse program is focused on behavior modification for diabetics with other chronic conditions, members who have diabetes, but no catastrophic conditions are flagged separately.

4. Trigger type: This field represents the reason members are brought into the predictive modeling queue. Those with inpatient episodes require special counseling and reminder messages on how they can stay away from further hospitalizations. Further, they are a lot more receptive to behavioral intervention messages.

5. Data availability: It goes without saying that models must take into account available data assets.

Feature subset selection: For each leaf, we perform feature optimization to select the best feature subset at the point of diminishing returns.

a. Feature correlation: In order to minimize redundancy and feature dimension, we combine highly correlated features ($\rho \geq 0.9$) using principal component analysis, where $$\rho_{ij} = \frac{E[(x_i - \mu_i)(x_j - \mu_j)]}{\sigma_i \sigma_j}, \rho_{ii} = 1.$$

b. Feature ranking: The purpose of feature ranking is to investigate the level of contribution of each feature to the overall predictive accuracy. If features are completely orthogonal (i.e., $\rho_{ij}=0, i \neq j$), then feature ranking degenerates into marginal or one-dimensional feature ranking using a number of appropriate metrics, such as Fisher's discriminant ratio, multi-modal overlap (MOM) measure, divergence, Bhattacharyya distance (Kil and Shin, 1996). If features are not orthogonal, we can use stochastic or combinatorial optimization algorithms.

Learning: Learning can take the form of regression (continuous dependent variable, such as future cost) or classification (discrete dependent variable, such as identifying top 20% users in future cost). The dependent variables can be clinically or actuarially oriented. We use the following learning algorithms:

a. Multivariate linear regression $$(MVLR): y = a_0 + \sum_{n=1}^{N} a_n x_n$$

b. Bayesian regularization network (BRN): BRN can be used for both regression and classification (Foresee and Hagan, 1997).

Scoring: Using the learned parameter database, we now score an unknown batch of population using multiple learning algorithms.

Now we explore learning and scoring of one such embodiment as shown in FIG. 2. For FIG. 2, the following reference numbers are used: 1—input of fused features, those being all available medical and pharmacy data and demographic data; 2—feature subset selection; 3—learn or score decision?; 4—learn path; 5—MVLR learning; 6—BRN learning; 7—learned database; 8—score path; 9—MVLR scoring; 10—BRN scoring; 11—mean operator; 12—clinical condition summary; and, 13—final score and condition report.

Before discussing in detail, the following table provides detail on the 30 nodes in the hierarchical tree network.

| Leaf ID | Years Humana member | Category Flag | Diabetes | Trigger type | Data Asset |
|---|---|---|---|---|---|
| 1 | <0.5 | Yes | N/A | N/A | Rx + Med |
| 2 | <0.5 | Yes | N/A | N/A | Rx only |
| 3 | <0.5 | Yes | N/A | N/A | Med only |
| 4 | <0.5 | No | Yes | Rx | Rx + Med |
| 5 | <0.5 | No | Yes | Rx | Rx only |
| 6 | <0.5 | No | Yes | Rx | Med only |
| 7 | <0.5 | No | Yes | IP | Rx + Med |
| 8 | <0.5 | No | Yes | IP | Rx only |
| 9 | <0.5 | No | Yes | IP | Med only |
| 10 | <0.5 | No | No | Rx | Rx + Med |

-continued

| Leaf ID | Years Humana member | Category Flag | Diabetes | Trigger type | Data Asset |
|---|---|---|---|---|---|
| 11 | <0.5 | No | No | Rx | Rx only |
| 12 | <0.5 | No | No | Rx | Med only |
| 13 | <0.5 | No | No | IP | Rx + Med |
| 14 | <0.5 | No | No | IP | Rx only |
| 15 | <0.5 | No | No | IP | Med only |
| 16 | ≧0.5 | Yes | N/A | N/A | Rx + Med |
| 17 | ≧0.5 | Yes | N/A | N/A | Rx only |
| 18 | ≧0.5 | Yes | N/A | N/A | Med only |
| 19 | ≧0.5 | No | Yes | Rx | Rx + Med |
| 20 | ≧0.5 | No | Yes | Rx | Rx only |
| 21 | ≧0.5 | No | Yes | Rx | Med only |
| 22 | ≧0.5 | No | Yes | IP | Rx + Med |
| 23 | ≧0.5 | No | Yes | IP | Rx only |
| 24 | ≧0.5 | No | Yes | IP | Med only |
| 25 | ≧0.5 | No | No | Rx | Rx + Med |
| 26 | ≧0.5 | No | No | Rx | Rx only |
| 27 | ≧0.5 | No | No | Rx | Med only |
| 28 | ≧0.5 | No | No | IP | Rx + Med |
| 29 | ≧0.5 | No | No | IP | Rx only |
| 30 | ≧0.5 | No | No | IP | Med only |

In the above table, the leafs identified by 1-15 form a first set of nodes of members with enrollment less than 6 months and leafs 16-30 form a second set of nodes with enrollment ≦6 months. For the first set of nodes 1-15, leafs 1-3 form a first subset and leafs 4-15 form a second subset; leafs 4-6 form a first subsubset, leafs 7-9 form a second subsubset, leafs 10-12 form a third subsubset, and leafs 13-15 form a fourth subsubset. For the second set of nodes 16-30, leafs 16-18 form a first subset and leafs 19-30 form a second subset; leafs 19-21 form a first subsubset, leafs 22-24 form a second subsubset, leafs 25-27 form a third subsubset, and leafs 28-30 form a fourth subsubset.

1. In order for the predictive model to deal with every conceivable situation, as shown above, we create a hierarchical tree network as a function of the following five stratification variables, resulting in 30 nodes or leaves:
   a. Enrollment duration: How long a member has been with Humana. As shown above, members are divided into those who have been with Humana for 0-0.5 years and those who have been with Humana more than 0.5 years.
   b. Catastrophic condition: Does a member have a high-severity clinical condition? If a member has any of the following, the category flag is yes, otherwise no.
      i. Cancer.
      ii. End-stage disease (kidney or liver failure).
      iii. Transplant.
      iv. Rare disease.
      v. HIV.
      vi. CAD+CHF+hypertension.
   c. Diabetes flag, yes or no. If the member has a catastrophic condition in b. above, they are in leafs 1-3 or 16-18 and diabetes flag does not affect.
   d. Trigger type: Either a new Rx claim or inpatient admit.
   e. Available data: Rx only, medical only, or both.

As an example, from the above table and above description of the 30 nodes, we see that if John Smith has been with Humana for 9 months and has a catastrophic condition, he will fall into leaf #16 provided that he has both pharmacy and medical benefits. On the other hand, if Nancy Doe has been with Humana for 12 months, doesn't have any catastrophic condition, but is diabetic, and has an inpatient trigger, then she will fall into leaf #22 assuming that she has both medical and pharmacy benefit plans covered by Humana. It is also seen that only members who have a catastrophic condition or who have either an inpatient admission trigger or a prescription trigger will be assigned to one of the thirty nodes.

2. For each leaf, we perform feature optimization to find an optimal subset using the add-on combinatorial optimization.
3. During learning, we train both multivariate linear regression (MVLR) and Bayesian regularization network (BRN) algorithms. The learned parameters are stored in a local database. The two learning algorithms are selected to cope with both data-mismatch and model-mismatch errors commonly encountered in real-world conditions. Model-mismatch errors occur when a learning algorithm is too simple to adequately model the complex relationship between inputs and outputs. On the other hand, data-mismatch errors occur when a super-tuned learning algorithm can't cope with differences in data characteristics between training data and test data.
4. During scoring, both learning algorithms provide their estimates on the future health status of a member.
5. A simple arithmetic mean operator outputs the final score, which is then combined with a member's clinical condition summary in a report format. The clinical condition report consists of up to top five MCC conditions, trigger type, trigger date, scoring date, person key, insulin, oral or both code if diabetic, and maternity flag.

For each leaf described above, a separate learning takes place for a structurally homogeneous population segment that belongs to that leaf. For example, we obtain the following statistics for leaves 16-18:
   1. Performance measured in $$R^2 = 1 - \frac{\text{var}(y - \hat{y})}{\text{var}(y)},$$

where $y$ and $\hat{y}$ refer to the actual and predicted outputs, respectively, and $\text{var}(\bullet)$ denotes the variance operator:
   a. Rx+med: 0.41/0.39 (BRN/MVLR)
   b. Rx only: 0.24/0.18
   c. Med only: 0.36/0.35
   2. The top five features are as follows:
   a. Rx+med
      i. Square root of the total prior paid amount
      ii. Mean utilization for other inpatient facilities
      iii. Trend in prior paid amount over time
      iv. Fluctuations in paid amount—the more consistent, the easier to predict.
      v. Costs associated with rare diseases, such as multiple sclerosis, hemophiliacs, etc.
   b. Rx only
      i. Non-zero Rx cost duration
      ii. The number of unique drugs taken
      iii. Ace drug cost
      iv. The ratio of Rx chronic cost to Rx total cost—the higher the ratio, the easier it is to predict.
      v. GPI drug class id
   c. Med only
      i. Square root of the most recent 6-month prior paid amount
      ii. Mean utilization for other inpatient facilities
      iii. The number of unique diagnosis in primary ICD-9 iv. Mean of the Major Clinical Condition (MCC) cost per month v. Mean paid amount for inpatient physician claims 3. During scoring, we compute a large number of features for each member, find the leaf #she belongs to, filter the feature subset we need for the selected leaf, load learning parameters associated with the two learning algorithms for that leaf, and generate two outputs from MVLR and BRN. For consensus between the two learning algorithms, we take an arithmetic mean. For MVLR, the learning parameters consist of normalization and regression coefficients. For BRN, the learning parameters comprise network architecture structure, optimization function, and weight/bias values for each network node and connection.

4. As an output, we append to the mean score each person's clinical conditions, weather map, trigger information, and other eligibility information. The member weather map provides a representation of member costs over a specified time period for that member's pharmacy and/or medical claims. Mapping ICD9 codes to major clinical conditions, the medical cost information can be shown for the different major clinical condition categories (such as, for example, coronary artery disease, congestive heart failure, other heart disease, circulatory, cancer) and subsets and subsubsets thereof (such as, for example, major clinical condition coronary artery disease has subclasses coronary artery bypass graft, percutaneous transluminal coronary angioplasty, myocardial infarction, angina, other ischemic heart disease, coronary atherosclerosis, and hyperlipidemia). Drug codes are also mapped to the various major clinical conditions and subsets and subsubsets thereof. The member weather map can also show member utilization and medical claim costs by place of treatment (such as, for example, hospital inpatient, hospital emergency, physician office visit) over the same specified time period.

We next provide additional algorithmic details.

Bayesian Regularization Network:

The traditional feedforward neural network learns a highly nonlinear relationship between inputs and outputs iteratively using multiple feedforward connected neurons that perform weighted arithmetic summing and nonlinear activation. Unfortunately, in the presence of data mismatch, which is sometimes known as "novel" inputs, performance has been found to be lacking robustness. This is where regularization plays an important role.

Regularization means finding meaningful approximate solutions, not meaningless accurate ones (Neumaier, 1998). A famous regularization method in linear algebra is called diagonal loading, which is also known as the Tikhonov regularization.

If we are interested in finding a solution x in y=Ax, the well-known standard L-2 solution is $\hat{x}=(A'A)^{-1}A'y$. For an ill-posed problem, where the pseudo inverse $A^+=(A'A)^{-1}A'$ doesn't exist (one can verify this using the singular value decomposition), a meaningful, good, approximate solution is $\hat{x}=(A'A+\sigma^2 I)^{-1}A'y$, where we add a small amount to each diagonal term for regularization. This feature is built into our multivariate Gaussian classification algorithm.

Similarly in learning, instead of using a traditional objective function that minimizes the mean-squared error (L-2 norm), one can use an optimization function conceptually similar to the Bayesian Information Criterion (BIC) or the minimum description length (Rissanen, 1989), which is in the form of $BIC \approx \log p(D|S,\hat{\theta}_s) - d/2 \log N$, where D and S refer to database and model structure, respectively. N is the sample size of the data while d is the number of parameters of the model S with $\hat{\theta}_s$ representing a set of parameters associated with a given model structure. Intuitively, this equation states that the objective function can be maximized by maximizing the explanation power of the model structure learned from data while simultaneously minimizing the model complexity.

In BRN, the objective function $J=\alpha E_{\|y-\hat{y}\|}+\beta E_{\|\omega\|}$, where $\alpha+\beta=1$. The first term in J is the well-known mean-squared prediction error while the second term represents the sum of squares of the network weights. If $\beta \gg \alpha$, learning will place much heavier emphasis on weight reduction at the expense of minimizing prediction errors with the resulting network response much smoother than otherwise. Under Gaussian assumptions, one can apply Bayes' rule to derive closed-form solutions for $\alpha$ and $\beta$ (Foresee and Hagan, 1997).

In short, BRN relies on the use of Bayesian regularization to avoid overfitting during learning while retaining the flexibility to learn and respond to novel patterns. In this case, we use three factors-error, network weights, and model complexity in terms of the actual feature dimension—in the objective function for greater robustness.

Linear Regression:

The function $$y = a_0 + \sum_{n=1}^{N} a_n x_n$$

can be implemented as follows:

$$\begin{bmatrix} y(1) \\ y(2) \\ \vdots \\ y(M) \end{bmatrix} = \begin{bmatrix} 1 & x_1(1) & \ldots & x_N(1) \\ 1 & x_1(2) & \ldots & x_N(2) \\ \vdots & \vdots & \ddots & \vdots \\ 1 & x_1(M) & \ldots & x_N(M) \end{bmatrix} \begin{bmatrix} a_0 \\ a_1 \\ \vdots \\ a_N \end{bmatrix} \leftrightarrow y = Xa$$

$$\hat{a} = X \backslash y \text{ or } \hat{a} = (X^t X + \sigma^2 I)^{-1} X^t y$$

$$\hat{y} = X\hat{a}$$

Again we use the Tikhonov regularization to find a robust solution to the matrix inversion problem.

We next summarize how we tackle the robustness issue. 1. Objective function that addresses prediction errors, model complexity, and model parameters. 2. Transformation of a dependent variable to reduce dynamic range and scale outrageous outliers, i.e., square root of cost instead of linear cost. 3. Performance analysis that includes five- or ten-fold cross validation and full-data-set training. 4. Multiple-model combining.

Implementation Example

Given the diversity of human disease progression, we expected a significant amount of data mismatch, implying that the learning algorithm must be robust against conditions not encountered during training. Further, we expected the problem to be nonlinear as in most real-world problems.

After careful consideration of a number of learning algorithms, we decided on a combination of multivariate linear regression and Bayesian regularization network (BRN), looking for a consensus between the two. Linear regression was chosen because of its robustness in the presence of data mismatch. Nonparametric and boundary-decision learning algorithms based on L-2 objective functions are notorious for generating wild guesses when forced to operate outside their comfort zone (i.e., extrapolation instead of interpolation in engineering).

Despite its robustness against data mismatch, linear regression runs out of breath when modeling complex, nonlinear relationships. To mask this shortcoming, we combine linear regression with Bayesian regularization network (BRN). Further, leveraging the concepts of regularization and BIC, we introduce an additional penalty term as a function of the model complexity so that we trade off the desire to minimize prediction errors during learning against the need for robustness against novel, unseen data through generalization.

Figure 3A:
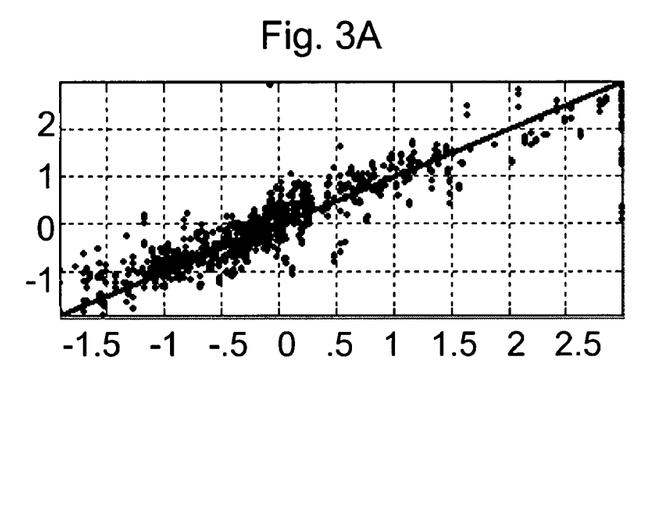
FIGS. 3A-H show the two selected learning algorithms (a combination of multivariate linear regression and Bayesian regularization network) in action.
Figure 3B:
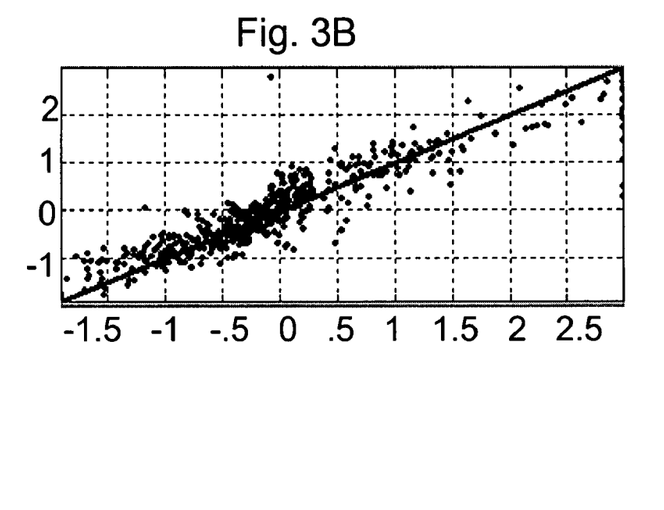
Figure 3C:
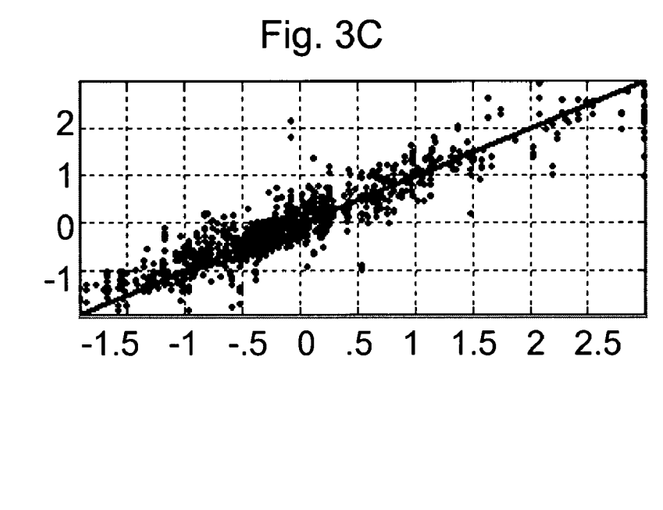
Figure 3D:
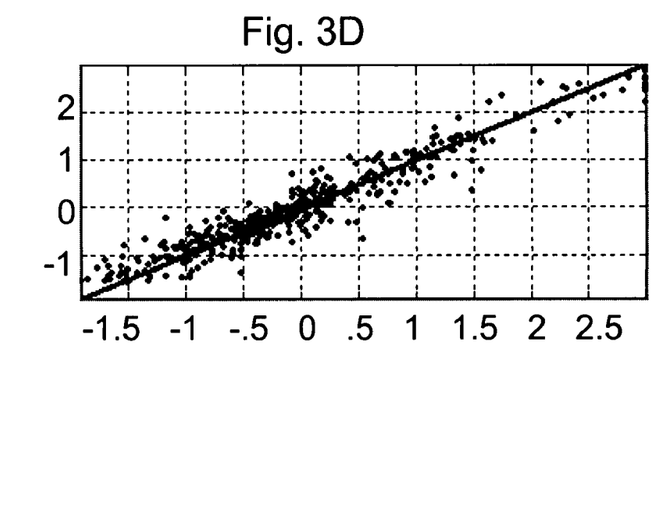
Figure 3E:
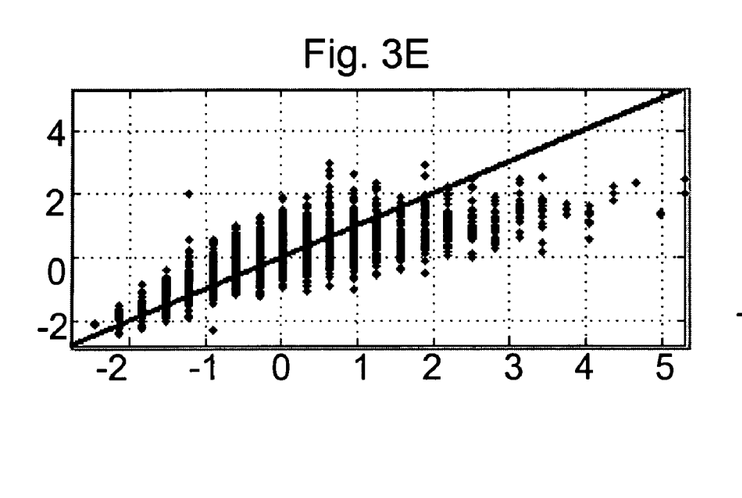
Figure 3F:
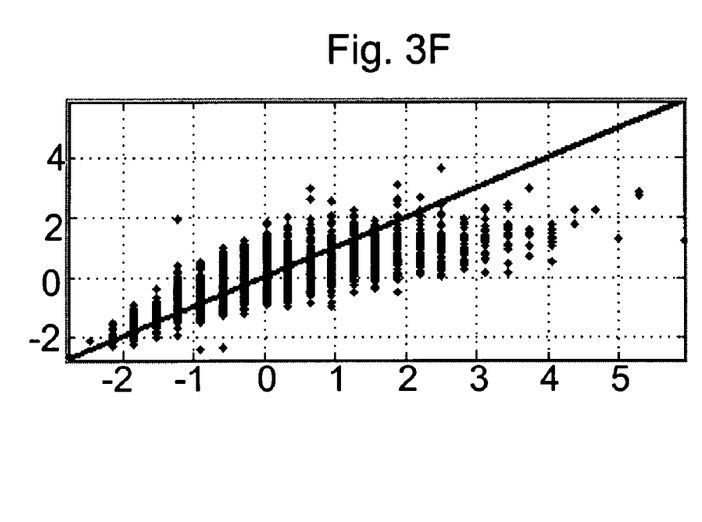
Figure 3G:
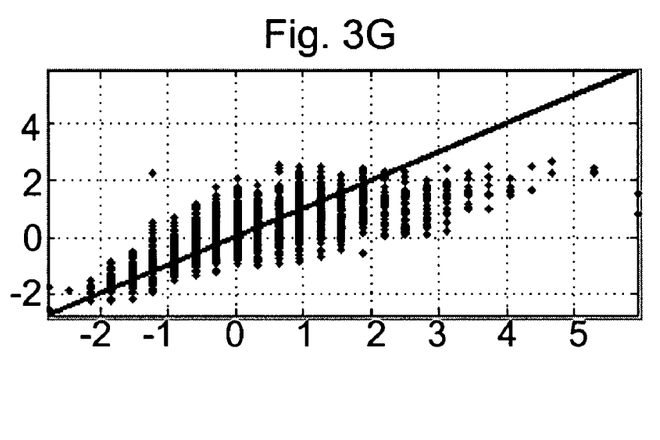
Figure 3H:
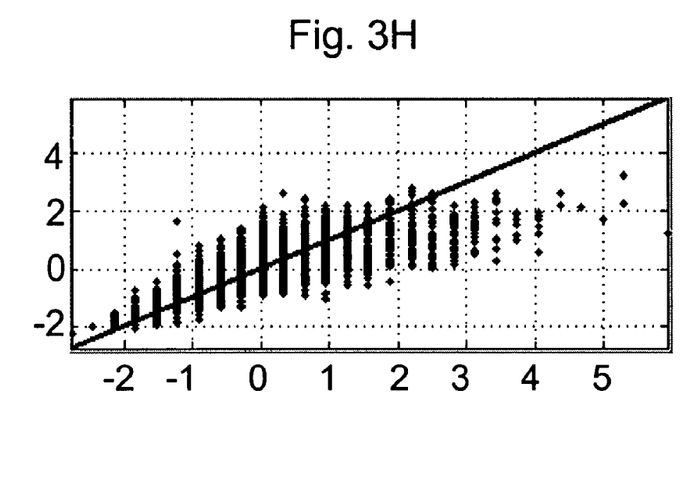
Figure 4A:
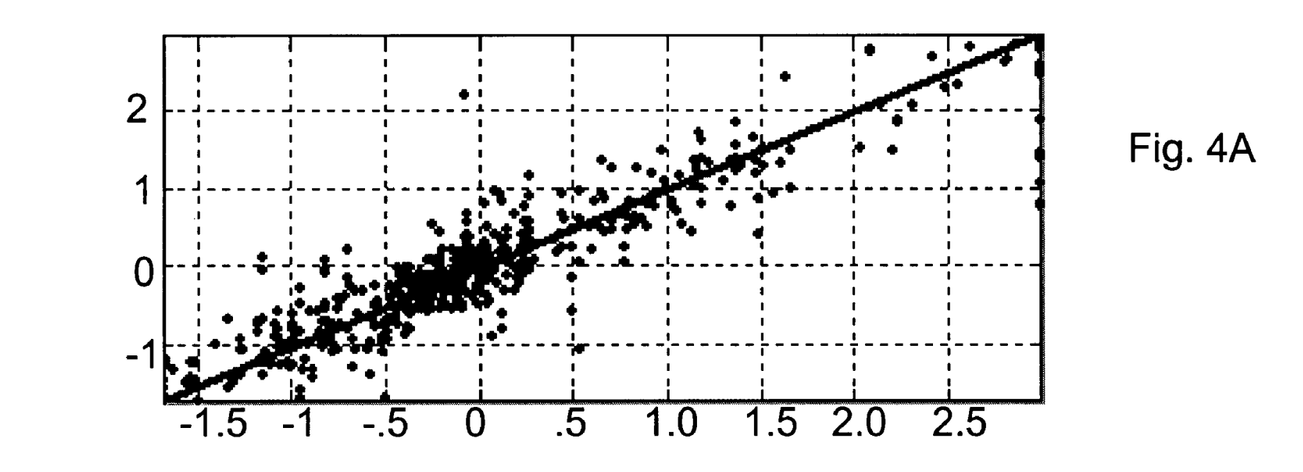
FIGS. 4A-B show a glimpse into the effect of memorization for a multilayer perceptron.
Figure 4B:
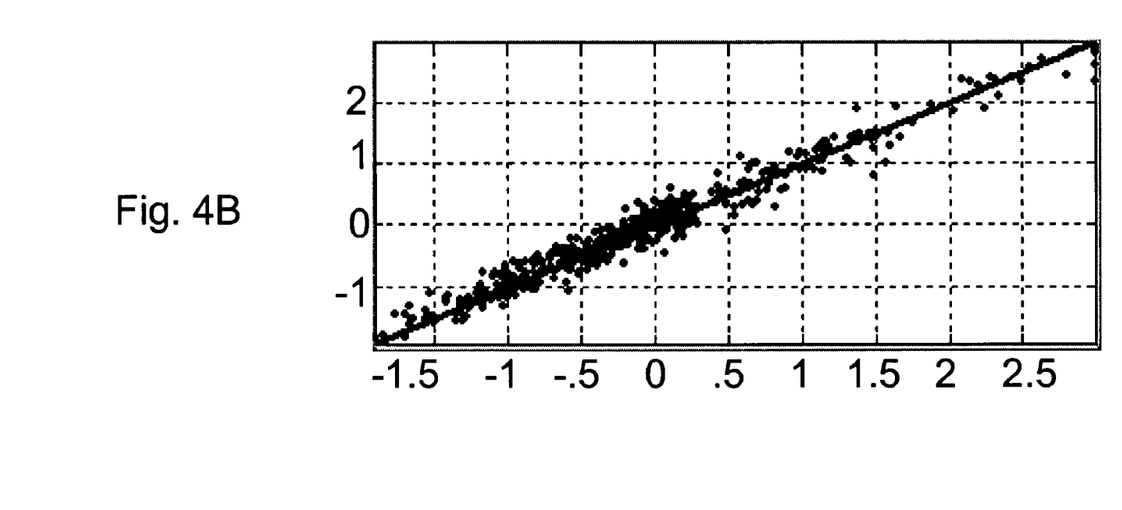

The robustness of learning can be ascertained by noting the differences in performance between random cross validation and full-data-set training, which is generally preferred in real-time implementation because one wants to model as much real data as possible. FIGS. 3A-H show the two selected learning algorithms in action with two different data sets. FIGS. 3A-B show linear regression for a first data set and FIGS. 3C-D show BRN for that data set. FIGS. 3B and 3D are for the full data set and FIGS. 3A and 3C are the cross validation. FIG. 3A graphs output predicted (y axis) versus actual (x axis) with $R_{sq}$=0.86358. FIG. 3B graphs output predicted (y axis) versus actual (x axis) with $R_{sq}$=0.83052. FIG. 3C graphs output predicted (y axis) versus actual (x axis) with $R_{sq}$=0.91497. FIG. 3D graphs output predicted (y axis) versus actual (x axis) with $R_{sq}$=0.92077. FIGS. 3E-F show linear regression for a second data set and FIGS. 3G-H show BRN for that data set. FIGS. 3F and 3H are for the full data set and FIGS. 3E and 3G are the cross validation. FIG. 3E graphs output predicted (y axis) versus actual (x axis) with $R_{sq}$=0.58165. FIG. 3F graphs output predicted (y axis) versus actual (x axis) with $R_{sq}$=0.56736. FIG. 3G graphs output predicted (y axis) versus actual (x axis) with $R_{sq}$=0.59826. FIG. 3H graphs output predicted (y axis) versus actual (x axis) with $R_{sq}$=0.59819. As expected, the performance discrepancies between full-data-set training and random cross-validated training on the two different data sets are small and even negative in some instances, which is a testament to learning robustness. FIG. 4A graphs output predicted (y axis) versus actual (x axis) with $R_{sq}$=0.90001. FIG. 4B graphs output predicted (y axis) versus actual (x axis) with $R_{sq}$=0.96846. In this case, the performance discrepancy is rather significant and, if this situation is observed with robust learning algorithms, the level of data mismatch is quite high.

If learning algorithms simply memorize the solution instead of generalizing, then we expect to see the performance discrepancy to be greater as shown in FIGS. 4A-B. FIGS. 4A-B show the effect of memorization for a multilayer perceptron. FIG. 4B is based on full data set training using a neural network that minimizes an L-2 objective function while FIG. 4A is based on cross validation.

Figure 5:
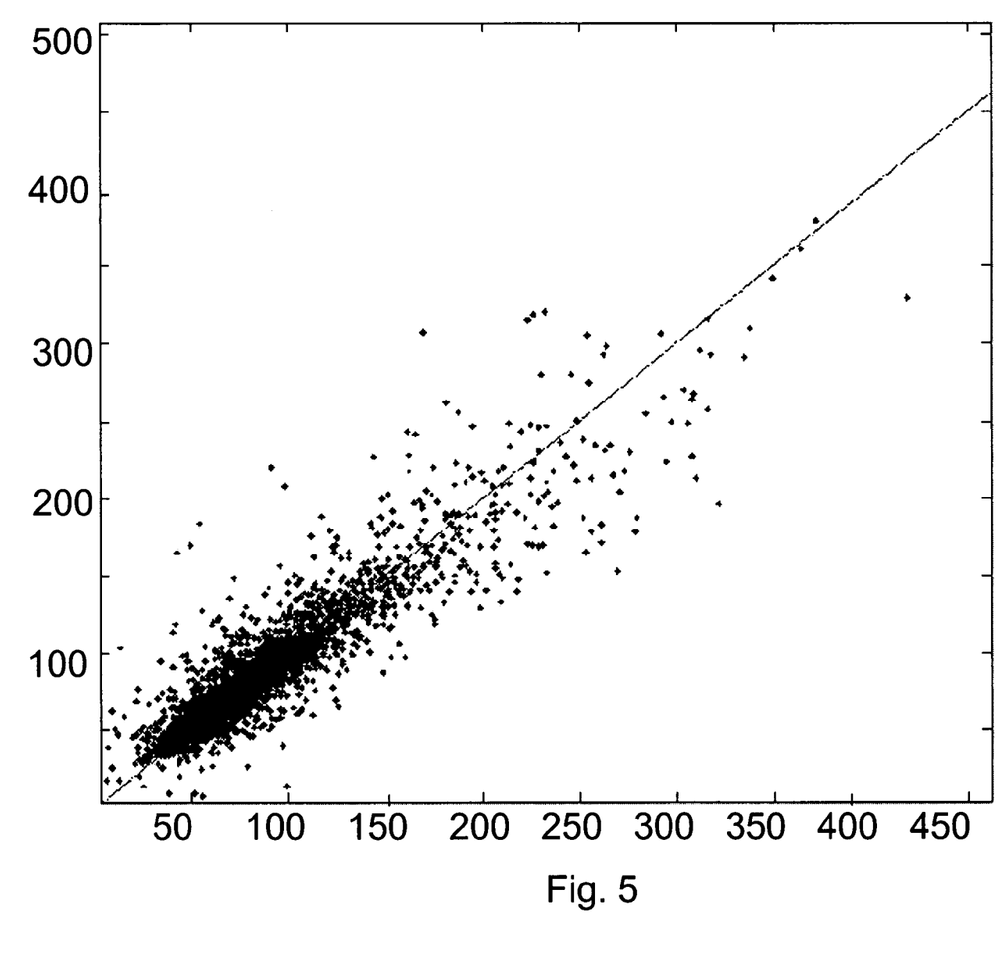
FIG. 5 shows that while the two learning algorithms, Bayesian regularization network (BRN) and Multivariate linear regression (MVLR), are generally in agreement, in some cases, they provide different answers as seen by numerous scatter points away from the line, which represents perfect agreement.

FIG. 5 graphs the Bayesian regularization network (BRN) prediction (y axis) versus the Multivariate linear regression (MVLR) prediction (x axis) and shows that while the two learning algorithms are generally in agreement, in some cases, they provide different answers as seen by numerous scatter points away from the line, which represents perfect agreement. Here, the predicted variable equals the square root of the future one-year cost (both medical and pharmacy) using the prior nine months of claims and demographic data.

In summary, we rely on the following criteria to ensure that our solutions are both accurate and robust: error minimization; model-complexity minimization; model-weight minimization for smooth, generalized responses; feature ranking to find the point of diminishing returns; minimization of discrepancy between full-data-set training and five-/ten-fold cross validations; and multiple-model combining.

As an implementation example of the hierarchical tree network with leaf-specific feature optimization, we now explore how some leaves behave differently.

For members with catastrophic conditions, many useful features come from cost trends associated with chronic conditions, such as end stage renal disease/chronic kidney disease, cancer, and rare disease. Another interesting feature deals with recent hospital outpatient trends, where dialysis is typically performed. Moreover, the ratio of medical to Rx cost is important since higher Rx cost with correspondingly low medical cost in this population segment is usually credited with better health management.

Interestingly, while not important for those with both medical and Rx benefits, for those with only Rx claims with Humana, both the quantity of pharmacy claims and the ratio of the cost for chronic Rx medication divided by the total Rx costs are important. That is, depending on the type of benefit plan one has, the feature optimization algorithm selects an optimal subset automatically.

On the other hand, diabetic members have numerous cost drivers, such as mental disorder (people recently diagnosed with chronic conditions tend to suffer from depression and other mental anxieties), vent, congestive heart failure, endocrine, digestive, and other complications. One such indicator is the number of different International Classification of Disease codes, or ICD codes, during the past nine months. ICD codes are often seen referred to as ICD9 codes, referring to the $9^{th}$ Revision of the codes.

Figure 6A:
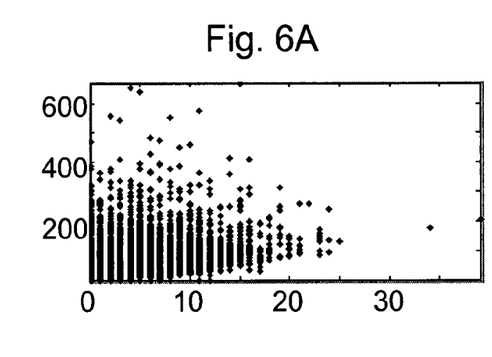
Figure 6B:
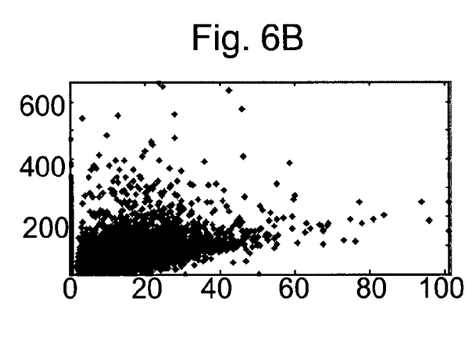
Figure 6C:
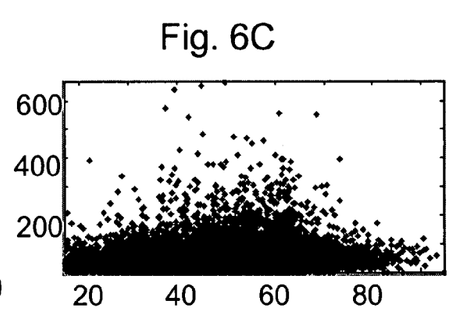
Figure 6D:
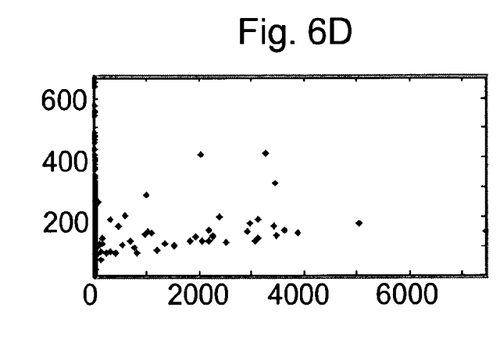
Figure 6E:
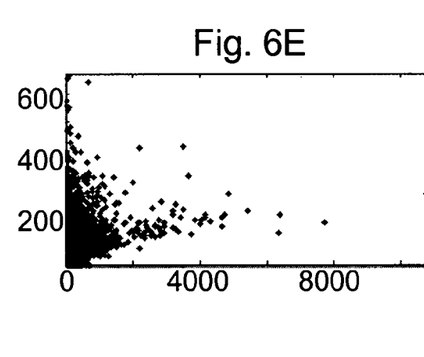
Figure 6F:
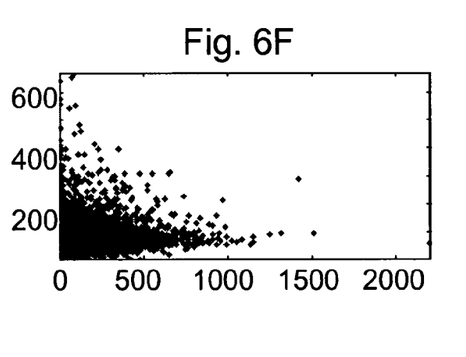

Nevertheless, there is no obvious rule of thumb that can be used a priori to guess which features would be more effective for a particular leaf. In order to investigate this matter, we explore a number of two-dimensional scatter plots of the square root of one-year future cost versus the following covariates as shown in FIGS. 6A-F: the number of unique drugs being taken (FIG. 6A); total Rx cost (FIG. 6B); age (FIG. 6C); transplant-related cost (FIG. 6D); chronic cost (FIG. 6E); and coronary artery disease (CAD) cost (FIG. 6F). If there is a simple linear relationship, one will see a straight, monotonically increasing line. Unfortunately, we do not see such an obvious trend with any of these features, indicating that there is no simple linear insight.

The first myth that is proven wrong is that the more drugs one takes, the more likely he or she will end up costing more in the future. FIG. 6A shows no such relationship. In FIG. 6B, the total Rx cost appears more promising, although we see a big blob in the beginning half (over 90% of the population) that shows a less-than-conclusive picture. FIG. 6C shows that the riskiest age group seems to be around the age of 50-65. One can also see in FIG. 6C that age is not useful in predicting the future cost. The same observation holds for both chronic costs in FIG. 6E and CAD costs in FIG. 6F. That is, having multiple chronic co-morbid conditions does not automatically lead to unpleasant future consequences. This observation summarizes difficulties inherent in building a predictive model for predicting future health status.

Therefore, instead of forcing our frequently wrong intuition on a predictive model or throwing everything (including many useless noisy ones) into the model, we construct a hierarchical tree network and let an optimization algorithm sort through a large number of features and select the best subset for each leaf. That is, we let the data tell us what to implement for each leaf.

The present invention includes a computer-based system for predicting a person's future health status comprising: a. a hierarchical tree network that assigns each member to one of thirty nodes as a function of the five stratification variables; b. feature-subset selection for each node using a number of stochastic and combinatorial optimization algorithms; c. separate learning and scoring modules depending on the operating mode; d. an arithmetic mean operator that seeks for consensus from the two learning algorithms; and e. a report generator that outputs pertinent parameters to aid clinical intervention. The five meaningful stratification variables are used in designing the hierarchical tree network so that a turnkey solution is delivered in terms of data and experience period requirements. That is, we don't have to worry about processing only those with at least six months of claims experience plus both medical and Rx data. Further, the two learning algorithms complement each other so that we operate in a robust subspace of the vector space comprising the model-mismatch-versus-data-mismatch and modeling-flexibility-versus-model-complexity spectra.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for predicting a person's future health status, comprising:
  a. establishing a hierarchical tree network that, for a plurality of members, assigns each member to at most only one of a plurality of nodes as a function of a plurality of stratification variables;
  b. providing to a computer based system, for said plurality of members and for each said member, member demographic data, available member medical claim data, and available member pharmacy claim data;
  c. a computer performing feature selection for each of said plurality of nodes to identify for each said node an optimal subset of features from a set comprising at least some of said member demographic data, said available member medical claim data, and said available member pharmacy claim data for all members assigned to that said node;
  d. a computer training a MVLR algorithm and a BRN algorithm using at least some of said member demographic data, said available member medical claim data, and said available member pharmacy claim data and storing learned parameters in a database to create a learned parameter database;
  e. using the learned parameter database and, for at least one said member, using that at least one said member's member demographic data, said available member medical claim data, and said available member pharmacy claim data, a computer calculating a MVLR future health status score using said MVLR algorithm and calculating a BRN future health status score using said BRN algorithm, and calculating an arithmetic mean of said MVLR future health status score and said BRN future health status score to determine a final score.

2. The method for predicting a person's future health status of claim 1, where, after determining the final score, the method further includes the step of producing a member clinical condition report, said member clinical condition report including member identification information and said final score.

3. The method for predicting a person's future health status of claim 2, where said member clinical condition report further includes said member's clinical condition data and at least a portion of any of said member's medical claim information and pharmacy claim information.

4. The method for predicting a person's future health status of claim 1, where in the step of establishing a hierarchical tree network, the plurality of stratification variables include at least some of a member's enrollment duration, a member's presence or lack of a catastrophic condition, a member's presence or lack of a diabetes flag, a member having a prescription trigger or an inpatient admission trigger, and a members claim data.

5. The method for predicting a person's future health status of claim 4, where, if said member's enrollment duration is less than six months, said member will be assigned to one of a first set of nodes; and, if said member's enrollment duration is at least six months, said member will be assigned to one of a second set of nodes.

6. The method for predicting a person's future health status of claim 5, where, if said member's enrollment duration is less than six months and if said member has the presence of a catastrophic condition, said member will be assigned to a first subset of said first set of nodes; where, if said member's enrollment duration is less than six months and if said member has the lack of a catastrophic condition, said member will be assigned to one of said first set of nodes not in said first subset of said first set of nodes, said one of said first set of nodes not in said first subset of said first set of nodes comprising a second subset of said first set of nodes; where, if said member's enrollment duration is at least six months and if said member has the presence of a catastrophic condition, said member will be assigned to a first subset of said second set of nodes; where, if said member's enrollment duration is at least six months and if said member has the lack of a catastrophic condition, said member will be assigned to one of said second set of nodes not in said first subset of said second set of nodes, said one of said second set of nodes not in said first subset of said second set of nodes comprising a second subset of said second set of nodes.

7. The method for predicting a person's future health status of claim 6, where, if said member's enrollment duration is less than six months and if said member has the lack of a catastrophic condition and if said member has the presence of a diabetic flag and if said member has a prescription trigger, said member is assigned to a first subsubset of said second subset of said first set of nodes; where, if said member's enrollment duration is less than six months and if said member has the lack of a catastrophic condition and if said member has the presence of a diabetic flag and if said member has an inpatient admission trigger, said member is assigned to a second subsubset of said second subset of said first set of nodes; where, if said member's enrollment duration is less than six months and if said member has the lack of a catastrophic condition and if said member has the lack of a diabetic flag and if said member has a prescription trigger, said member is assigned to a third subsubset of said second subset of said first set of nodes; where, if said member's enrollment duration is less than six months and if said member has the lack of a catastrophic condition and if said member has the lack of a diabetic flag and if said member has an inpatient admission trigger, said member is assigned to a fourth subsubset of said second subset of said first set of nodes; where, if said member's enrollment duration is at least six months and if said member has the lack of a catastrophic condition and if said member has the presence of a diabetic flag and if said member has a prescription trigger, said member is assigned to a first subsubset of said second subset of said second set of nodes; where, if said member's enrollment duration is at least six months and if said member has the lack of a catastrophic condition and if said member has the presence of a diabetic flag and if said member has an inpatient admission trigger, said member is assigned to a second subsubset of said second subset of said second set of nodes; where, if said member's enrollment duration is at least six months and if said member has the lack of a catastrophic condition and if said member has the lack of a diabetic flag and if said member has a prescription trigger, said member is assigned to a third subsubset of said second subset of said second set of nodes; and, where, if said member's enrollment duration is at least six months and if said member has the lack of a catastrophic condition and if said member has the lack of a diabetic flag and if said member has an inpatient admission trigger, said member is assigned to a fourth sub subset of said second subset of said second set of nodes.

8. The method for predicting a person's future health status of claim 7, where said first subset of said first set of nodes, said first subsubset of said second subset of said first set of nodes, said second subsubset of said second subset of said first set of nodes, said third subsubset of said second subset of said first set of nodes, said fourth subsubset of said second subset of said first set of nodes, said first subset of said second set of nodes, said first subsubset of said second subset of said second set of nodes, said second subsubset of said second subset of said second set of nodes, said third subsubset of said second subset of said second set of nodes, and said fourth subsubset of said second subset of said second set of nodes, each comprise a first node where said member has both pharmacy and medical claim data, a second node where said member has medical claim data only, and a third node where said member has pharmacy claim data only.

9. The method for predicting a person's future health status of claim 4, where said member will have the presence of a catastrophic condition if said member has at least one of any cancer, an end-stage disease, a transplant, a rare disease, HIV, a combination of coronary artery disease plus chronic heart failure plus hypertension.

10. The method for predicting a person's future health status of claim 1, where said plurality of nodes of said hierarchical tree network comprises thirty nodes,
   a. a first node for any member with an enrollment duration of less than six months, the presence of a catastrophic condition, and both pharmacy and medical claim data;
   b. a second node for any member with an enrollment duration of less than six months, the presence of a catastrophic condition, and pharmacy claim data only;
   c. a third node for any member with an enrollment duration of less than six months, the presence of a catastrophic condition, and medical claim data only;
   d. a fourth node for any member with an enrollment duration of less than six months, the lack of a catastrophic condition, the presence of a diabetes trigger, the presence of a prescription trigger, and both pharmacy and medical claim data;
   e. a fifth node for any member with an enrollment duration of less than six months, the lack of a catastrophic condition, the presence of a diabetes trigger, the presence of a prescription trigger, and pharmacy claim data only;
   f. a sixth node for any member with an enrollment duration of less than six months, the lack of a catastrophic condition, the presence of a diabetes trigger, the presence of a prescription trigger, and medical claim data only;
   g. a seventh node for any member with an enrollment duration of less than six months, the lack of a catastrophic condition, the presence of a diabetes trigger, the presence of an inpatient admission trigger, and both pharmacy and medical claim data;
   h. an eighth node for any member with an enrollment duration of less than six months, the lack of a catastrophic condition, the presence of a diabetes trigger, the presence of an inpatient admission trigger, and pharmacy claim data only;
   i. a ninth node for any member with an enrollment duration of less than six months, the lack of a catastrophic condition, the presence of a diabetes trigger, the presence of an inpatient admission trigger, and medical claim data only;
   j. a tenth node for any member with an enrollment duration of less than six months, the lack of a catastrophic condition, the lack of a diabetes trigger, the presence of a prescription trigger, and both pharmacy and medical claim data;
   k. an eleventh node for any member with an enrollment duration of less than six months, the lack of a catastrophic condition, the lack of a diabetes trigger, the presence of a prescription trigger, and pharmacy claim data only;
   l. a twelfth node for any member with an enrollment duration of less than six months, the lack of a catastrophic condition, the lack of a diabetes trigger, the presence of a prescription trigger, and medical claim data only;
   m. a thirteenth node for any member with an enrollment duration of less than six months, the lack of a catastrophic condition, the lack of a diabetes trigger, the presence of an inpatient admission trigger, and both pharmacy and medical claim data;
   n. a fourteenth node for any member with an enrollment duration of less than six months, the lack of a catastrophic condition, the lack of a diabetes trigger, the presence of an inpatient admission trigger, and pharmacy claim data only;
   o. a fifteenth node for any member with an enrollment duration of less than six months, the lack of a catastrophic condition, the lack of a diabetes trigger, the presence of an inpatient admission trigger, and medical claim data only;
   p. a sixteenth node for any member with an enrollment duration of at least six months, the presence of a catastrophic condition, and both pharmacy and medical claim data;
   q. a seventeenth node for any member with an enrollment duration of at least six months, the presence of a catastrophic condition, and pharmacy claim data only;
   r. an eighteenth node for any member with an enrollment duration of at least six months, the presence of a catastrophic condition, and medical claim data only;
   s. a nineteenth node for any member with an enrollment duration of at least six months, the lack of a catastrophic condition, the presence of a diabetes trigger, the presence of a prescription trigger, and both pharmacy and medical claim data;
   t. a twentieth node for any member with an enrollment duration of at least six months, the lack of a catastrophic condition, the presence of a diabetes trigger, the presence of a prescription trigger, and pharmacy claim data only;
   u. a twenty-first node for any member with an enrollment duration of at least six months, the lack of a catastrophic condition, the presence of a diabetes trigger, the presence of a prescription trigger, and medical claim data only;
   v. a twenty-second node for any member with an enrollment duration of at least six months, the lack of a catastrophic condition, the presence of a diabetes trigger, the presence of an inpatient admission trigger, and both pharmacy and medical claim data;

w. a twenty-third node for any member with an enrollment duration of at least six months, the lack of a catastrophic condition, the presence of a diabetes trigger, the presence of an inpatient admission trigger, and pharmacy claim data only;
x. a twenty-fourth node for any member with an enrollment duration of at least six months, the lack of a catastrophic condition, the presence of a diabetes trigger, the presence of an inpatient admission trigger, and medical claim data only;
y. a twenty-fifth node for any member with an enrollment duration of at least six months, the lack of a catastrophic condition, the lack of a diabetes trigger, the presence of a prescription trigger, and both pharmacy and medical claim data;
z. a twenty-sixth node for any member with an enrollment duration of at least six months, the lack of a catastrophic condition, the lack of a diabetes trigger, the presence of a prescription trigger, and pharmacy claim data only;
aa. a twenty-seventh node for any member with an enrollment duration of at least six months, the lack of a catastrophic condition, the lack of a diabetes trigger, the presence of a prescription trigger, and medical claim data only;
bb. a twenty-eighth node for any member with an enrollment duration of at least six months, the lack of a catastrophic condition, the lack of a diabetes trigger, the presence of an inpatient admission trigger; and both pharmacy and medical claim data;
cc. a twenty-ninth node for any member with an enrollment duration of at least six months, the lack of a catastrophic condition, the lack of a diabetes trigger, the presence of an inpatient admission trigger, and pharmacy claim data only; and,
dd. a thirtieth node for any member with an enrollment duration of at least six months, the lack of a catastrophic condition, the lack of a diabetes trigger, the presence of an inpatient admission trigger, and medical claim data only.

11. The method for predicting a person's future health status of claim 10, where, after determining the final score, the method further includes the step of producing a member clinical condition report, said member clinical condition report including member identification information and said final score.

12. The method for predicting a person's future health status of claim 11, where said member clinical condition report further includes said member's clinical condition data and at least a portion of any of said member's medical claim information and pharmacy claim information.

13. The method for predicting a person's future health status of claim 10, where said member will have the presence of a catastrophic condition if said member has at least one of any cancer, an end-stage disease, a transplant, a rare disease, HIV, a combination of coronary artery disease plus chronic heart failure plus hypertension.

* * * * *

UNITED STATES PATENT AND TRADEMARK OFFICE
CERTIFICATE OF CORRECTION

| | | |
|---|---|---|
| PATENT NO. | : 7,725,329 B2 | Page 1 of 1 |
| APPLICATION NO. | : 11/114692 | |
| DATED | : May 25, 2010 | |
| INVENTOR(S) | : David H. Kil and David B. Pottschmidt | |

It is certified that error appears in the above-identified patent and that said Letters Patent is hereby corrected as shown below:

Column 7, line 27, "$\leq 6$" should be changed to -- $\geq 6$ --.

Signed and Sealed this
Fifteenth Day of February, 2011

David J. Kappos
*Director of the United States Patent and Trademark Office*